(12) United States Patent
Warzywoda et al.

(10) Patent No.: US 7,494,792 B2
(45) Date of Patent: Feb. 24, 2009

(54) PROCESS FOR THE PRODUCTION OF CELLULOLYTIC AND HEMICELLULOLYTIC ENZYMES USING DISTILLATION RESIDUES FROM THE ETHANOLIC FERMENTATION OF ENZYMATIC HYDROLYZATES OF (LIGNO)CELLULOSIC MATERIALS

(75) Inventors: Michel Warzywoda, Rueil Malmaison (FR); Daniel Ballerini, Saint Germain en Laye (FR); Frédéric Monot, Nanterre (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 333 days.

(21) Appl. No.: 11/349,938

(22) Filed: Feb. 9, 2006

(65) Prior Publication Data
US 2006/0177917 A1 Aug. 10, 2006

(30) Foreign Application Priority Data
Feb. 9, 2005 (FR) .................................. 05 01371

(51) Int. Cl.
C12P 7/06 (2006.01)
C12P 7/10 (2006.01)
C12P 19/14 (2006.01)
C12N 9/42 (2006.01)
C12N 1/16 (2006.01)

(52) U.S. Cl. ..................... 435/165; 435/69.1; 435/99; 435/161; 435/174; 435/209; 435/254.1

(58) Field of Classification Search ....................... None
See application file for complete search history.

(56) References Cited

U.S. PATENT DOCUMENTS

| 3,990,944 A | 11/1976 | Gauss et al. |
| 3,990,945 A * | 11/1976 | Huff et al. ................... 435/99 |
| 4,762,788 A | 8/1988 | Warzywoda et al. |
| 6,723,549 B2 * | 4/2004 | Miettinen-Oinonen et al. ... 435/204 |
| 7,323,326 B2 * | 1/2008 | Miettinen-Oinonen et al. ... 435/209 |
| 2003/0113734 A1 | 6/2003 | Dunn-Coleman et al. |
| 2004/0265953 A1 * | 12/2004 | Harman et al. ............. 435/69.1 |

FOREIGN PATENT DOCUMENTS

WO   WO 03052055   6/2003

OTHER PUBLICATIONS

Chahal Parminder S et al: "Production of cellulose in solid-state fermentation with Trichoderma reesei MCG 80 on wheat straw" Appliced Biochemistry and Biotechnology, vol. 57*58, No. 0, 1996, pp. 433-442, XP008054568.

Warzywoda M et al: "Production and Characterization of Cellulolytic Enzymes From Trichoderma-Reesei Grown on Various Carbon Sources" Bioresource Technology, vol. 39, No. 2, 1992, pp. 125-130, XP008054567.

* cited by examiner

Primary Examiner—Herbert J. Lilling
(74) Attorney, Agent, or Firm—Millen, White, Zelano & Branigan, P.C.

(57) ABSTRACT

A process for producing cellulolytic and/or hemicellulolytic enzymes uses the residue from the ethanolic fermentation of enzymatic hydrolyzates of cellulosic or ligno-cellulosic materials. This process may be integrated into a process for the production of ethanol from cellulosic or ligno-cellulosic materials which comprises the following steps:
1) chemical and/or physical pre-treatment of a cellulosic or ligno-cellulosic substrate;
2) enzymatic hydrolysis of the pre-treated substrate using cellulolytic and/or hemicellulolytic enzymes;
3) ethanolic fermentation, by a suitable alcohologenic microorganism, of the hydrolyzate from step (2) and production of a fermentation must; and
4) separation of the alcohologenic microorganism used in step (3), separation/purification of the ethanol and production of an aqueous phase constituting a residue;
and in which said residue serves for the production of the cellulolytic and/or hemicellulolytic enzymes used in step 2).

19 Claims, 1 Drawing Sheet

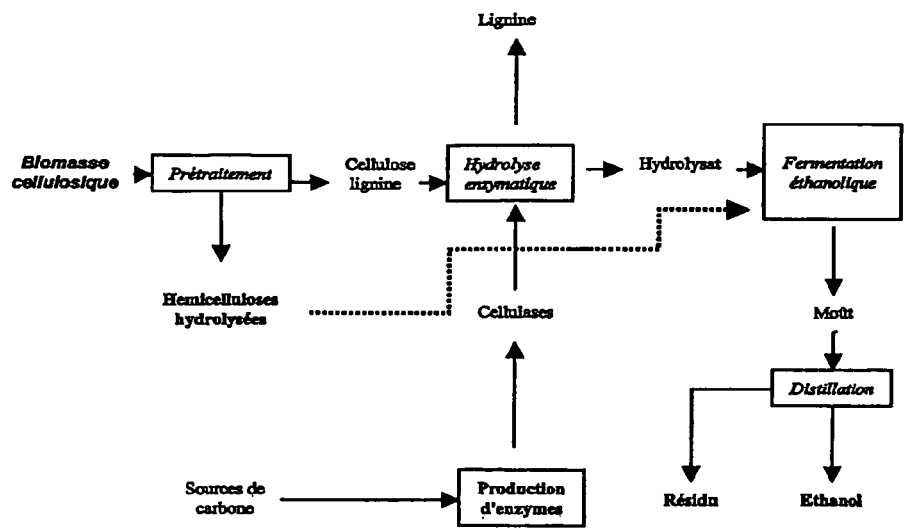

FIG. 1

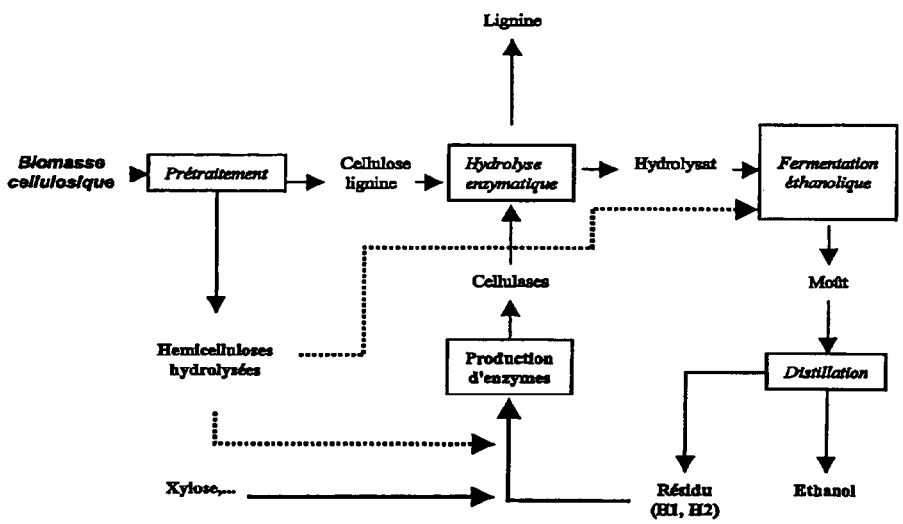

FIG. 2

KEY TO FIG 1 & FIG 2:

| French | English |
|---|---|
| Lignine | Lignin |
| Biomasse cellulosique | Cellulosic biomass |
| Prétraitement | Pre-treatment |
| Hydrolyse enzymatique | Enzymatic hydrolysis |
| Hydrolysat | Hydrolysate |
| Fermentation éthanolique | Ethanolic fermentation |
| Hemicelluloses hydrolysées | Hydrolyzed hemicelluloses |
| Moût | Must |
| Sources de carbone | Carbon sources |
| Production d'enzymes | Enzyme production |
| Résidu | Residue |

US 7,494,792 B2

PROCESS FOR THE PRODUCTION OF CELLULOLYTIC AND HEMICELLULOLYTIC ENZYMES USING DISTILLATION RESIDUES FROM THE ETHANOLIC FERMENTATION OF ENZYMATIC HYDROLYZATES OF (LIGNO)CELLULOSIC MATERIALS

BACKGROUND OF THE INVENTION

1. Field of the Invention

The present invention relates to the production of cellulolytic and/or hemicellulolytic enzymes, in particular in the context of the production of ethanol from cellulosic or ligno-cellulosic materials.

2. Description of Related Art

Since the 1970s, the transformation of ligno-cellulosic biomass to ethanol after hydrolysis of the constituent polysaccharides to fermentable sugars has formed the basis of a great deal of work.

Deciduous tree wood and cereal straw are the most widely used substrates. They are mainly constituted by about 40% to 50% of cellulose, 20% to 25% of hemi-cellulose and 15% to 25% of lignin.

Other resources, dedicated forest cultures, residues from alcohologenic plants, sugar refineries and cereal processors, residues from the paper industry and transformation products from cellulosic or ligno-cellulosic materials can be used.

Of those three polymers, cellulose, hemi-cellulose and lignin, cellulose is the principal source of fermentable sugars for fermenting to ethanol as it is constituted by glucose, which is readily fermented to ethanol by *Saccharomyces cerevisiae* in proven, high performance industrial processes. The pentoses contained in hemi-celluloses are not efficiently converted into ethanol. Other microorganisms form the genii *Saccharomyces, Pichia, Candida, Pachysolen, Zymomonas, Klebsiella, Escherichia*, may be selected to upgrade the monomeric sugars derived from the biomass to ethanol.

The process for transforming ligno-cellulosic materials to ethanol (see FIG. 1) comprises a physico-chemical pre-treatment step followed by an enzymatic or chemical hydrolysis step, a step for ethanolic fermentation of the sugars released and a step for recovering ethanol.

The pre-treatment step is aimed at liberating the sugars contained in the hemi-celluloses in the form of monomers, essentially pentoses, such as xylose and arabinose, and hexoses, such as galactose, mannose and glucose, and to improve the accessibility of the cellulose gummed into the lignin and hemi-cellulose matrix. A number of techniques exist: acid boiling, alkaline boiling, steam explosion, organosolv processes, etc. The pre-treatment efficacy is measured by the degree of hemi-cellulose recovery and by the susceptibility of the cellulosic residue to hydrolysis. Mild acid pre-treatments and steam explosion are the best techniques. They allow complete recovery of pentoses and good accessibility of the cellulose to hydrolysis.

The cellulosic residue is hydrolyzed, either by the acid method or by the enzymatic method using cellulolytic and/or hemicellulolytic enzymes. Microorganisms such as fungi from the genii *Trichoderma, Aspergillus, Penicillium* or *Schizophyllum*, or anaerobic bacteria, for example from the genus *Clostridium*, produce such enzymes, contain mainly cellulases and xylanases, suitable for complete hydrolysis of polymers constituting the plants.

The acidic method, carried out with a strong acid, in particular sulphuric acid, is effective but requires large quantities of chemicals (acid then base for neutralization). Enzymatic hydrolysis does not suffer from that disadvantage; it is carried out under mild conditions and is effective. In contrast, the cost of enzymes is still very high. For this reason, a great deal of work has been carried out to reduce the cost: increasing the production of enzymes in the first place, by selecting hyperproductive strains and by improving the fermentation conditions, reducing the quantity of enzymes in the hydrolysis, and in the second place, by optimizing the pre-treatment phase or by improving the specific activity of said enzymes. During the last decade, most studies have concerned understanding the mechanisms of the action of cellulases and the expression of enzymes to cause the enzymatic complex which is the most appropriate for hydrolysis of the ligno-cellulosic substrates to be excreted by modifying the strains with molecular biology tools.

The most commonly used microorganism for the production of cellulases is the fungus *Trichoderma reesei*. Wild type strains are able to excrete, in the presence of an inducing substrate, for example cellulose, the enzymatic complex considered to be the best adapted to cellulose hydrolysis. The enzymes of the enzymatic complex contain three major types of activities: endoglucanases, exoglucanases and cellobiases. Other proteins with properties which are vital to the hydrolysis of ligno-cellulolytic materials are also produced by *Trichoderma reesei*, for example xylanases. The presence of an inducer substrate is vital to the expression of cellulolytic and/or hemicellulolytic enzymes. The nature of the carbon-containing substrate has a large influence on the composition of the enzymatic complex. This is the case with xylose which, associated with a carbon-containing inducer substrate such as cellulose or lactose, can significantly improve xylanase activity.

Conventional genetic mutation techniques have enabled strains of *Trichoderma reesei* which are hyperproductive in cellulases to be produced, such as the MCG77 (Gallo, U.S. Pat. No. 4,275,167 A), MCG 80 (Allen A L and Andreotti R E, Biotechnol-Bioeng 1982, 12, 451-459, 1982), RUT C30 (Montenecourt, B S and Eveleigh D E, Appl Environ Microbiol 1977, 34, 777-782) and CL847 (Durand et al, 1984, Proc Colloque SFM, "Génétique des microorganismes industriels", Paris, H HESLOT Ed, pp 39-50). The improvements have produced hyperproductive strains which are less sensitive to the catabolic repression on monomer sugars, for example glucose, compared with wild type strains.

Recombinant strains have also been obtained from strains of Qm9414, RutC30, CL847 *Trichoderma reesei* by cloning heterologous genes, for example *Aspergillus niger* invertase, to diversify the source of carbon necessary for the production of cellulases, and/or over-express cellobiase to improve the enzymatic hydrolysis yield, cellobiases being considered to be limiting enzymes in the reaction. Said strains have conserved their hyperproductivity and aptitude for cultivation in the fermenter.

The process for producing cellulases by *Trichoderma reesei* has formed the subject matter of major improvements with a view to extrapolation to the industrial scale.

To obtain good enzyme productivity, it is necessary to add a source of carbon which can be rapidly assimilated to allow the *Trichoderma reesei* to grow and an inducer substrate which allows expression of cellulases and secretion into the culture medium. Cellulose may play both roles; however, it is difficult to use on an industrial scale and has been replaced by soluble sources of carbon, glucose, xylose or lactose, lactose also acting as an inducer substrate. Other soluble sugars such as cellobiose and sophorose have been described as inducers, but they are too expensive to be used on an industrial scale. However, it has been established that the production of cellulases by *Trichoderma reesei* with soluble substrates is far inferior to those obtained on cellulose in a batch process. This is due to the repressor effect of readily assimilatable sugars at high concentrations. Continuously supplying soluble carbon-containing substrates lifts catabolic repression by limiting the residual concentration in the cultures and optimizing the quantity of sugar, producing a better yield and better enzymatic productivity (see French Patent No.2 555 603 B).

In an industrial process for the production of cellulolytic enzymes, lactose remains one of the most suitable substrates and one of the cheapest; however, it is still expensive and represents about a third of the cost price of the enzymes. Despite all of the progress made, the cost of enzymes when transforming cellulosic biomass to ethanol remains high, at 30% to 50%; further, when using lactose as the carbon source for the production of cellulases, the process is dependent on an external source of carbon. For this reason, the use of carbon-containing substrates from spinning, for example hydrolyzed hemi-celluloses, is an important advance if the source of the inducing carbon is readily available.

BRIEF SUMMARY OF THE INVENTION

The present invention concerns the use of the residue obtained after ethanolic fermentation of monomer sugars of enzymatic hydrolyzates of cellulosic biomass, as the source of inducing carbon for the production of cellulolytic and/or hemicellulolytic enzymes with cellulolytic fungus strains, in particular those from the genus *Trichoderma reesei*.

BRIEF DESCRIPTION OF THE DRAWING FIGURES

The drawing FIG. 1 shows a flowchart for the conventional process for transforming ligno-cellulosic materials to ethanol.

The drawing FIG. 2 shows a flowchart for the production of cellulolytic and/or hemicellulolytic enzymes from ethanolic fermentation residues in accordance with the invention.

DETAILED DESCRIPTION OF THE INVENTION

The present invention provides a process for producing cellulolytic and/or hemicellulolytic enzymes by a cellulolytic microorganism comprising using the residue from the ethanolic fermentation of enzymatic hydrolyzates of cellulosic or ligno-cellulosic materials.

This process may be integrated into a process for the production of ethanol from cellulosic or ligno-cellulosic materials which comprises the following steps:
1) chemical and/or physical pre-treatment of a cellulosic or ligno-cellulosic substrate;
2) enzymatic hydrolysis of the pre-treated substrate using cellulolytic and/or hemicellulolytic enzymes;
3) ethanolic fermentation, by a suitable alcohologenic microorganism, of the hydrolyzate from step (2) and production of a fermentation must; and
4) separation of the alcohologenic microorganism used in step (3), separation/purification of the ethanol and production of an aqueous phase constituting a residue;

and in which said residue serves for the production of the cellulolytic and/or hemicellulolytic enzymes used in step 2).

The principal source of carbon may be a soluble industrial sugar, for example glucose, lactose or xylose, or an extract of the hemicellulosic fraction in the form of monomers from the pre-treated biomass. The residue may also be used as a total carbon source, i.e. for the growth of the microorganism and induction of the expression system. This carbon source can be used by genetically enhanced strains and in particular by recombinant strains.

One aim of the invention is to propose a source of inducing carbon or total carbon which is readily available, to produce cellulolytic and/or hemicellulolytic enzymes with activities appropriate for the hydrolysis of cellulosic biomass. The flowchart for the production of cellulolytic and/or hemicellulolytic enzymes from ethanolic fermentation residues in accordance with the invention is shown in FIG. 2. This invention can also upgrade internally non upgradable ethanol co-products.

A first step in pre-treating the biomass is carried out to improve the susceptibility of the enzymatic hydrolysis fraction of the cellulosic fraction and hydrolyze the hemicellulosic fraction. The most appropriate method is steam explosion under acidic conditions. Under optimum conditions, from 150° C. to 250° C. over several minutes, it transforms the hemicelluloses to monomers while minimizing losses, particularly of furfural, xylose being the major sugar. The sugars which are released may be extracted by washing in the aqueous phase; the solid residue from extraction then contains only cellulose and lignin. After extraction, the sugars which are released are used for the production of enzymes as the principal source of carbon or upgraded to ethanol by fermentation with suitable strains.

The cellulose fraction, which may or may not be free of the hydrolyzed hemicellulosic fraction and possibly of lignin, is hydrolyzed by the cellulolytic and/or hemicellulolytic enzymes produced by the specialized strains, *Trichoderma reesei* cellulases being the most effective and the most appropriate when the carbon-containing substrates derive from cellulosic or ligno-cellulosic biomass. The material to be hydrolyzed is suspended in an aqueous phase in an amount of 6% to 25% of dry matter, preferably 10% to 20%; the pH is adjusted to between 4 and 5.5, preferably 4.8 to 5.2, and the temperature is adjusted to between 40° C. and 60° C., preferably between 45° C. and 50° C. The hydrolysis reaction is started by adding cellulases; the quantity normally used is 10 to 30 mg of excreted proteins per gram of pre-treated substrate. The reaction generally takes 15 to 48 hours depending on the efficacy of the pre-treatment, the composition of the mixture of cellulases and the quantity of enzymes added. The reaction is followed by assaying the sugars which are released, in particular glucose. The sugar solution is separated from the non hydrolyzed solid fraction, essentially constituted by lignin, by filtration or centrifuging; it is used for ethanolic fermentation. When the cellulosic fraction has been freed of hydrolyzed hemicelluloses at the treatment step, glucose is the major sugar withdrawn in this step. The residue from ethanolic fermentation, after separating the ethanol, is used as a source of inducing carbon or as a principal source of carbon for the production of enzymes. The concentration of said residue is adjusted to obtain the concentration of source carbon which is best suited to the process for producing cellulolytic and/or hemicellulolytic enzymes.

In general, the ethanol is separated from the fermentation must by distillation and the residue is constituted of distillation slops.

The strains used for the production of cellulolytic and/or hemicellulolytic enzymes are strains of fungi from the *Trichoderma, Aspergillus, Penicillium* or *Schizophyllum* genii, preferably from the *Trichoderma reesei* species. The best performing industrial strains are strains belonging to the species *Trichoderma reesei*, modified to improve the cellulolytic and/or hemicellulolytic enzymes by mutation-selection processes, such as the IFP CL847 strain (French Patent No. 2 555 803 B); strains improved by genetic recombination techniques may also be used.

These strains are cultivated in stirred and aerated fermenters under conditions compatible with their growth and the production of enzymes. Depending on its nature, the carbon-containing substrate selected to produce the biomass is introduced into the fermenter before sterilization or it is sterilized separately and introduced into the fermenter after sterilizing the latter to produce an initial concentration of 20 to 35 g/l; the inducing source does not need to be added in this phase. An aqueous solution containing the substrate selected for the production of enzymes is prepared in a concentration of 200-250 g/l; this solution must contain the inducer substrate. It is injected after exhaustion of the initial substrate in order to supply an optimized quantity, between 35 and 45 mg/g of cells (fed batch). The residual concentration of sugar in the culture medium is less than 1 g/l during this fed batch phase.

The entire disclosure of all applications, patents and publications, cited above and below, and of corresponding French Patent application 05/01371, filed Feb. 9, 2005, are hereby incorporated by reference.

In the following examples, Examples 1 to 3 are given by way of indication and Examples 4 and 5 illustrate the invention.

EXAMPLES

Example 1

Production of Enzymes on Lactose

The production of cellulases was carried out in a mechanically stirred fermenter. The medium had the following composition: KOH, 1.66 g/l; 85% $H_3PO_4$, 2 ml/l; $(NH_4)SO_4$, 2.8 g/l; $MgSO_4,7H_2O$, 0.6 g/l; $CaCl_2$, 0.6 g/l; $MnSO_4$, 3.2 mg/l; $ZnSO_4,7H_2O$, 2.8 mg/l; $CoCl_2$, 4.0 mg/l; $FeSO_4,7H_2O$, 10 mg/l, Corn Steep, 1.2 g/l, anti-foaming agent, 0.5 ml/l.

The fermenter containing 1.75 l of mineral medium and 70 g of lactose was sterilized at 120° C., then seeded with 0.25 liters of a liquid pre-culture of the CL847 *Trichoderma reesei* strain. The pre-culture medium, supplemented with 5 g/l potassium phthalate to control the variations in pH, was identical to that of the fermenter. The pre-culture fungus was grown on lactose to a concentration of 30 g/l. The growth period for the inoculum was 2 to 3 days and was carried out at 27° C. to 30° C. on a shaker table.

After 46 hours growth, the initial substrate from the fermenter was exhausted and the 250 g/l lactose solution was continuously injected at a flow rate of 4.5 ml/h to a time period of 142 hours.

The temperature was kept at 27° C. during the growth phase of the biomass, then at 25° C. until the end of the culture. The pH was adjusted to 5 during the growth phase, then to 4 up to the end of culture by adding an ammoniacal solution which supplied the nitrogen necessary for the synthesis of excreted proteins. The dissolved oxygen content was kept above 15% to 20% by adjusting aeration and stirring.

Enzyme production was followed by assaying extracellular proteins using the Folin (Lowry) method after separating from mycelium by filtration or centrifuging. The cellulolytic activity was determined using the filter paper activity (FPU: filter paper unit) method for overall activity and cellobiase activity, considered to limit enzymatic hydrolysis of the ligno-cellulosic biomass. The FPU activity was measured on Whatman N° 1 paper at an initial concentration of 50 g/l; the test sample of the enzymatic solution to be analyzed was determined which liberated the equivalent of 2 g/l of glucose (colorimetric assay) in 60 minutes. The cellobiase activity was measured on cellobiose in a concentration of 20 mM; the amount of sample which liberated 0.5 g/l of glucose (enzymatic assay) in 30 minutes was determined.

The activities in U/ml are expressed in micromoles of glucose liberated per minute and per milliliter of enzymatic solution.

Analyses of the final must produced the following results:

| Substrate consumed, g/l | 79.6 |
| Biomass, g/l | 13.5 |
| Proteins, mg/ml | 37.8 |
| PFU, U/ml | 22.1 |
| Cellobiases, U/ml | 25.2 |

Example 2

Production of Enzymes on Xylose

The enzyme production was carried out under the same conditions as in Example 1.

The fermenter containing 1.75 l of mineral medium with 40 g of pure xylose was seeded with 0.25 liters of a liquid pre-culture of the CL847 *Trichoderma reesei* strain. The carbon-containing substrate of the pre-culture was glucose in a concentration of 20 g/l. After 27 hours growth, after exhaustion of the initial substrate, the 200 g/l xylose solution was continuously injected at a flow rate of 5 ml/h to a time period of 164 hours.

Analyses of the final must produced the following results:

| Substrate consumed, g/l | 63.7 |
| Biomass, g/l | 15.3 |
| Proteins, mg/ml | 6.1 |
| PFU, U/ml | 1.7 |
| Cellobiases, U/ml | 1.9 |

Example 3

Production of Enzymes on a 25%-75% Respectively Lactose-Xylose Mixture

In this example, lactose was used as an inducer substrate and injected solely at the enzyme production phase after exhaustion of the initial xylose.

Fermentation was carried out under the conditions described in Example 2. The substrate solution injected for the production of enzymes was replaced by a mixture of lactose and xylose in a concentration of 200 g/l, the concentration of lactose being 50 g/l. Injection was stopped after 164 hours had passed.

Analyses of the final must produced the following results:

| Substrate consumed, g/l | 62.7 |
| Biomass, g/l | 11.9 |
| Proteins, mg/ml | 34.2 |
| PFU, U/ml | 10.1 |
| Cellobiases, U/ml | 8.7 |

Example 4

Production of Enzymes on Xylose Using the Residue Produced By Ethanolic Fermentation of a Partial Enzymatic Hydrolyzate of a Treated and Depentosed Cellulosic Material as an Inducing Source Fermentation was carried out under the conditions described in Example 2. Biomass was batch produced with 20 g/l of xylose. Enzymes were produced in a fed batch with a solution prepared from a residue into which xylose had been added. The solution of residue, with reference numeral H1, was prepared as follows:

6 kg of moist solid material obtained after treatment of wheat straw by steam explosion under acidic conditions and extracting pentoses, namely 1.4 kg of dried and washed material, was taken up in 0.75 liters of 0.5 M sodium acetate buffer at a pH of 4.8 and 0.75 liters of a solution of commercially available cellulases, namely 30 g of proteins. After enzymatic hydrolysis for 24 hours, carried out in a mechanically stirred reactor and kept at 50° C., the suspension was separated by centrifuging. The recovered liquid fraction contained 92 g/l of glucose, 10.3 g/o of xylose, 1.0 g/l of arabinose. Ethanolic fermentation was carried out on said fraction using *Saccharomyces cerevisiae*. The inoculum, in a volume of 0.4 l, was prepared in a stirred flask on glucose using baker's yeast. The hydrolyzate glucose was completely fermented to ethanol. The must obtained was freed of proteins and yeast by heating to 100° C. and centrifuging. After concentration under vacuum, 0.85 l of ethanol-free slop H1 was obtained. the substrate solution, with a volume of 1.5 l, used for the production of enzyme, was prepared from this slop supplemented with xylose to obtain a final concentration of carbon-containing substrate of 200 g/l. Fermentation was carried out under the conditions described in Examples 1 to 3. Fermentation was stopped after 136 hours.

Analyses of the final must produced the results shown in the table below. The proteins were precipitated with trichloroacetic acid to avoid the undesirable color reaction linked to impurities in the residue.

| | |
|---|---|
| Substrate consumed, g/l | 59.0 |
| Biomass, g/l | 12.0 |
| Proteins, mg/ml | 33.6 |
| PFU, U/ml | 10.5 |
| Cellobiases, U/ml | 4.5 |

Example 5

Production of Enzymes on Xylose Using the Residue Produced By Ethanolic Fermentation of a Full Hydrolyzate of a Treated and Depentosed Cellulosic Material as an Inducing Source As described in Example 4, biomass was batch produced with 20 g/l of xylose. Enzymes were produced in a fed batch with a solution of substrate prepared from slop to which xylose had been added. In the present case, the solution of slop, with reference numeral H2, was prepared as described for H1, but hydrolysis was extended to 48 hours with an addition of enzymes identical to the initial addition after 24 hours of hydrolysis. The hydrolyzate contained 110.8 g/l of glucose, 11.8 g/l of xylose. The slop H2, after eliminating ethanol and concentrating, was used to prepare 1.5 l of a substrate solution containing 200 g/l of total sugars. Fermentation was carried out under the conditions of Example 4; fermentation was stopped after 158 hours.

Analyses of the final must produced the following results:

| | |
|---|---|
| Substrate consumed, g/l | 62.5 |
| Biomass, g/l | 14.5 |
| Proteins, mg/ml | 28.0 |
| PFU, U/ml | 10.0 |
| Cellobiases, U/ml | 4.7 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. In a fermentation process for producing cellulolytic and/or hemicellulolytic enzymes by a cellulolytic microorganism in the presence of inducing carbon, the improvement wherein the inducing carbon, comprises a residue from the ethanolic fermentation of enzymatic hydrolyzates of cellulosic or ligno-cellulosic materials, said residue being separated from ethanol.

2. A process according to claim 1, in which said residue comprises a source of carbon for growth of the cellulolytic microorganism and the production of cellulolytic and/or hemicellulolytic enzymes.

3. A process according to claim 1, in which the residue comprises a source of inducing carbon as a complement to other sources of carbon used for growth of the cellulolytic microorganism.

4. A process according to claim 1, in which the residue is the sole source of carbon for growth of the cellulolytic microorganism and production of cellulolytic and/or hemicellulolytic enzymes.

5. A process according to claim 1, in which the cellulolytic microorganism is a fungi from the genii *Trichoderma, Aspergillus, Penicillium* or *Schizophyllum*.

6. A process according to claim 5, in which the cellulolytic microorganism comprises the species *Trichoderma reesei*.

7. A process according to claim 1, in which the cellulosic or ligno-cellulosic materials comprise at least one of straw, wood, forest culture, alcohologenic residues from plants, sugar refineries and cereal producers, and residues from the paper industry.

8. A process according to claim 1, wherein said residue is obtained from a process for producing ethanol from cellulosic or ligno-cellulosic materials comprising:
   1) chemical and/or physical pre-treating of a cellulosic or lignocellulosic substrate;
   2) enzymatically hydrolyzing the pre-treated substrate using cellulolytic and/or hemicellulolytic enzymes;
   3) ethanolic fermenting by a suitable alcohologenic microorganism of the hydrolyzate from (2) and producing a fermentation must; and
   separating the alcohologenic microorganism of (3), separating/purifying the ethanol and obtaining an aqueous phase constituting said residue.

9. A process according to claim 8, in which, the ethanol is separated by distillation and the residue is constituted by distillation slops.

10. A process according to claim 2, in which the cellulolytic microorganism comprises fungi from at least one of the genii *Trichoderma, Aspergillus, Penicillium* or *Schizophyllum*.

11. A process according to claim 3, in which the cellulolytic microorganism comprises fungi from at least one of the genii *Trichoderma, Aspergillus, Penicillium* or *Schizophyllum*.

12. A process according to claim 4, in which the cellulolytic microorganism comprises fungi from at least one of the genii *Trichoderma, Aspergillus, Penicillium* and *Schizophyllum*.

13. A process according to claim 5, in which the cellulolytic microorganism comprises the species *Trichoderma reesei*.

14. A process according to claim 10, in which the cellulolytic microorganism comprises the species *Trichoderma reesei*.

15. A process according to claim 11, in which the cellulolytic microorganism comprises the species *Trichoderma reesei*.

16. A process according to claim 12, in which the cellulolytic microorganism comprises the species *Trichoderma reesei*.

17. A process according to claim 8, in which the cellulosic or ligno-cellulosic materials comprise at least one of straw, wood, forest culture, alcohologenic residues from plants, sugar refineries and cereal producers, and residues from the paper industry.

18. A process according to claim 8, further comprising producing said cellulolytic and/or hemicellulolytic enzymes of step (2), by a fermentation step wherein said residue provides inducing carbon.

19. A process according to claim 8, in which, the ethanol is separated by distillation and the residue is constituted of distillation slops.

* * * * *

UNITED STATES PATENT AND TRADEMARK OFFICE
CERTIFICATE OF CORRECTION

PATENT NO.       : 7,494,792 B2                                       Page 1 of 1
APPLICATION NO.  : 11/349938
DATED            : February 24, 2009
INVENTOR(S)      : Michel Warzywoda et al.

It is certified that error appears in the above-identified patent and that said Letters Patent is hereby corrected as shown below:

Column 10, line 17 reads "A process according to Claim 8, in which, the ethanol is" should read --A process according to Claim 18, in which, the ethanol is--

Signed and Sealed this

Twelfth Day of May, 2009

JOHN DOLL
*Acting Director of the United States Patent and Trademark Office*